(12) United States Patent
Huang et al.

(10) Patent No.: US 9,178,164 B2
(45) Date of Patent: Nov. 3, 2015

(54) ORGANIC COMPOUND AND ORGANIC ELECTROLUMINESCENT DEVICE EMPLOYING THE SAME

(71) Applicants: INDUSTRIAL TECHNOLOGY RESEARCH INSTITUTE, Hsinchu (TW); National Tsing Hua University, Hsinchu (TW)

(72) Inventors: Heh-Lung Huang, New Taipei (TW); Cheng-An Wu, New Taipei (TW); Chien-Hong Cheng, Hsin-Chu (TW)

(73) Assignees: INDUSTRIAL TECHNOLOGY RESEARCH INSTITUTE, Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/490,232

(22) Filed: Sep. 18, 2014

(65) Prior Publication Data

US 2015/0001521 A1  Jan. 1, 2015

Related U.S. Application Data

(63) Continuation-in-part of application No. 13/243,552, filed on Sep. 23, 2011, now abandoned.

(30) Foreign Application Priority Data

Aug. 5, 2011  (TW) .............................. 100127919 A

(51) Int. Cl.
*H01L 51/00* (2006.01)
*C07D 403/14* (2006.01)
*H01L 51/50* (2006.01)

(52) U.S. Cl.
CPC .......... *H01L 51/0067* (2013.01); *C07D 403/14* (2013.01); *H01L 51/0072* (2013.01);
(Continued)

(58) Field of Classification Search
None
See application file for complete search history.

(56) References Cited

U.S. PATENT DOCUMENTS 6,126,046 A  10/2000  Baculy 7,223,484 B2  5/2007  Stossel et al.
(Continued)

FOREIGN PATENT DOCUMENTS

CN  101679383 A  3/2010
JP  2005-112765 A  4/2005
(Continued)

OTHER PUBLICATIONS

Chinese Office Action for Appl. No. 201110235841.7 dated Apr. 9, 2014.
(Continued)

*Primary Examiner* — J. L. Yang
(74) *Attorney, Agent, or Firm* — Birch, Stewart, Kolasch & Birch, LLP

(57) ABSTRACT

Organic compounds and organic electroluminescence devices employing the same are provided. The organic compound has a chemical structure represented below:

wherein, $R^1$ are independently a hydrogen, or $C_{1-8}$ alkyl; and $R^2$ is a hydrogen, hydroxy, or $C_{1-8}$ alkoxy. The organic compounds have a high triplet energy ($tE_g$) gap and apt to transmit the energy to a guest emitter.

7 Claims, 1 Drawing Sheet

(52) U.S. Cl.
CPC ......... *H01L51/0081* (2013.01); *H01L 51/0085* (2013.01); *H01L 51/5016* (2013.01); *H01L 2251/308* (2013.01)

(56) References Cited

U.S. PATENT DOCUMENTS

| | | |
|---|---|---|
| 7,911,132 B2 | 3/2011 | Noguchi et al. |
| 2007/0252516 A1 | 11/2007 | Kondakova et al. |
| 2008/0286607 A1* | 11/2008 | Nomura et al. ............... 428/690 |

FOREIGN PATENT DOCUMENTS

| | | |
|---|---|---|
| JP | 2009-35524 A | 2/2009 |
| JP | 2009-215333 A | 9/2009 |
| TW | 200726317 A | 7/2007 |
| TW | 200732452 A | 9/2007 |
| TW | 200909416 A | 3/2009 |
| TW | 201043627 A | 12/2010 |
| WO | WO 2010/084729 A1 | 7/2010 |
| WO | WO 2011/010840 A1 | 1/2011 |

OTHER PUBLICATIONS

Chinese Office Action for Appl. No. 201110235841.7 dated Sep. 30, 2013.

Huang et al., "Dibenzothiophene/Oxide and Quinoxaline/Pyrazine Derivatives Serving as Electron-Transport Materials**," Advanced Functional Materials, vol. 16, 2006, pp. 1449-1456.

Huang et al., "Dipolar Dibenzothiophene S,S-Dioxide Derivatives Containing Diarylamine: Materials for Single-Layer Organic Light-Emitting Devices**," Advanced Materials, vol. 18, 2006, pp. 602-606.

Huang et al., "Organic electroluminescent derivatives containing dibenzothiophene and diarylamine segments," Journal of Materials Chemistry, vol. 15, Jun. 30, 2005, pp. 3233-3240.

Kim et al., "New host materials with high triplet energy level for blue-emitting electrophosphorescent device," Synthetic Metals, vol. 157, 2007, pp. 743-750.

Kim, M. K. et al, "A bipolar host containing 1,2,3-triazole for realizing highly efficient phosphorescent organic light-emitting diodes," New J. Chem., 2010, vol. 34, pp. 1317-1322.

Su et al., "Highly Efficient Organic Blue-and White-Light Emitting Devices Having a Carrier- and Exciton-Confining Structure for Reduced Efficiency Roll-Off**," Advanced Materials, vol. 20, 2008, pp. 4189-4194.

Su et al., "Pyridine-Containing Bipolar Host Materials for Highly Efficient Blue Phosphorescent OLEDs," Chemical Materials, vol. 20, Feb. 12, 2008, pp. 1691-1693.

\* cited by examiner

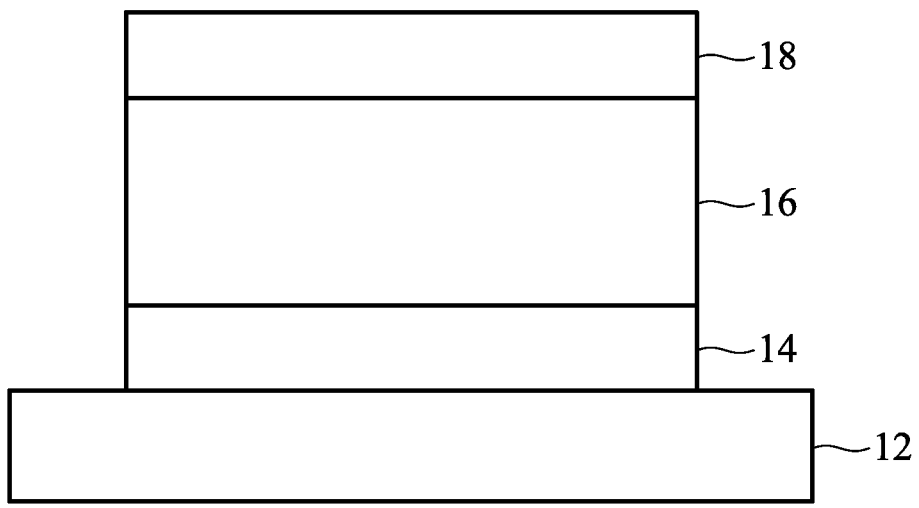

ORGANIC COMPOUND AND ORGANIC ELECTROLUMINESCENT DEVICE EMPLOYING THE SAME

CROSS REFERENCE TO RELATED APPLICATIONS

This application is a Continuation-In-Part of pending U.S. patent application Ser. No. 13/243,552, filed Sep. 23, 2011 and entitled "Organic compound and organic electroluminescent device employing the same", which claims priority of Taiwan Patent Application No. 100127919, filed on Aug. 5, 2011.

BACKGROUND

1. Field

The disclosure relates to an organic compound and organic electroluminescence device employing the same and, more particularly, to an organic compound serving as a host material and a phosphorescent organic electroluminescence device employing the same.

2. Description of the Related Art

Recently, with the development and wide application of electronic products, such as mobile phones, PDAs, and notebook computers, there has been increasing demand of flat display elements which consume less electric power and occupy less space. Organic electroluminescent devices are self-emitting and highly luminous, with wider viewing angles, faster response speeds, and simpler fabrication methods, making them an industry display of choice.

Generally, an organic electroluminescent device was composed of a light-emission layer sandwiched between a pair of electrodes. When an electric field was applied to the electrodes, the cathode injects electrons into the light-emission layer and the anode injects holes into the light-emission layer. When the electrons recombination with the holes in the light-emission layer, excitons were formed. Recombination of the electron and hole results in light emission.

Depending on the spin states of the hole and electron, the exciton which results from the hole and electron recombination can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent materials, in order to increase the emissive efficiency of the OLED.

In application of organic electroluminescent devices, phosphorescent guest materials have to be used in combination with host materials which has an energy gap matched therewith, thereby achieving optimal electroluminescent performance and quantum yield. Particularly, since blue and green host materials require larger differences of energy gap between the host and guest materials for electroluminescence, the host materials used in an phosphorescent OLED should have a shorter conjugated system. Further, in order to keep the key characteristics of the organic compound used in OLEDs (i.e. thermal-stability), the host material should also have larger molecular weight, resulting in difficulties for chemical structure designs.

Since conventional, commercially available phosphorescent host materials or phosphorescent host materials disclosed in prior art references merely have the moieties of carbazole or silyl benzene derivatives, the phosphorescent host materials exhibit inferior thermal stability, resulting in devices made therefrom to have low current density and high operating voltage.

BRIEF SUMMARY

An exemplary embodiment of an organic compound has a Formula (I), of:

Formula (I)
wherein, $R^1$ are independently a hydrogen, or $C_{1-8}$ alkyl; and $R^2$ is a hydrogen, hydroxyl, or $C_{1-8}$ alkoxy.

In another exemplary embodiment of the disclosure, an organic electroluminescence device is provided. The device includes: a pair of electrodes; and an electroluminescent element disposed between the pair of electrodes, wherein the electroluminescent element includes the aforementioned organic compound.

Yet another exemplary embodiment of the disclosure provides an organic electroluminescence device including an emission layer which includes a host material and a phosphorescent dopant. Particularly, the host material includes the aforementioned organic compound and the emission layer emits blue or green light under a bias voltage.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 shows a cross section of an organic electroluminescent device disclosed by an embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

Organic Compound

The disclosure provides organic compounds having a high triplet energy ($tE_g$) gap and apt to transmit the energy to a guest emitter. Therefore, the organic compounds of the disclosure are suitable as host material of blue or green phosphorescent organic electroluminescent devices, thereby increasing the efficiency thereof.

The disclosure provides an organic compound having a Formula (I), of:

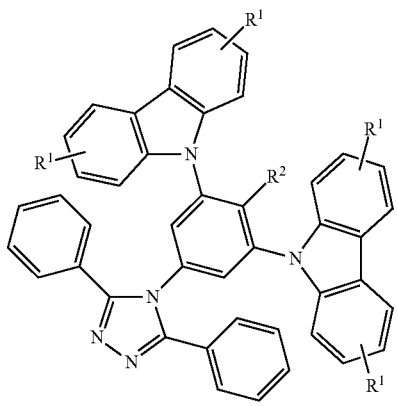

Formula (I)

wherein, $R^1$ are independently a hydrogen, or $C_{1-8}$ alkyl; and $R^2$ is a hydrogen, hydroxyl, or $C_{1-8}$ alkoxy.

In the structure of Formula (I), the moieties

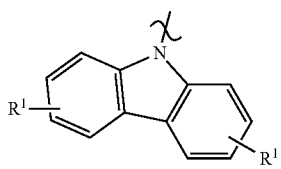

means that $R^1$ can be located at any one of the four substitutable positions of the benzene ring and the $R^1$ are independent. For example, $R^1$ can be each independently a methyl group, ethyl group, propyl group, isopropyl group, butyl group, tert-butyl group, pentyl group, or hexyl group. Further, $R^2$ can be methoxy group, ethoxy group, propoxy group, isopropoxy group, butoxy group, isobutoxy group, pentyloxy group, or hexyloxy group.

The organic compounds of Formula (I) of the disclosure have a high triplet energy ($tE_g$) gap and are apt to transmit the energy to a guest emitter. Further, in comparison with the conventional compound (represented by

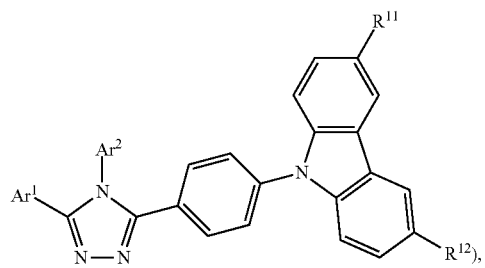

wherein $Ar^1$ and $Ar^2$ are phenyl or pyridine group, and $R^{11}$ and $R^{12}$ are hydrogen, alkyl group, hydroxyl group, or aryl group), since the organic compounds of Formula (I) of the disclosure have a triazole moiety bound to the benzene at the meta-position relative to a carbazole moiety resulting in a shorter conjugated system, the organic compounds of the disclosure are suitable for serving as a blue or green host material for a phosphorescent organic electroluminescent device. Moreover, the organic compounds of Formula (I) of the disclosure, in comparison with the conventional compound, are not apt to be crystallized after formation of a film by evaporation.

The organic compounds of the disclosure include the following compounds shown in Table 1. In addition, the contraction thereof are also named and shown in Table 1.

TABLE 1

| Example | Structures | Contraction |
| --- | --- | --- |
| 1 | 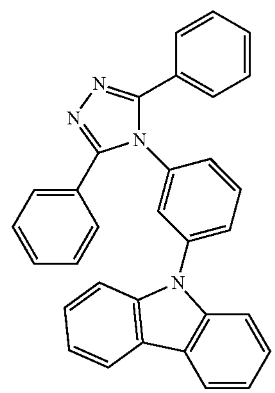 [SMILES: c1ccc(-c2nnc(-c3ccccc3)n2-c2cccc(-n3c4ccccc4c4ccccc43)c2)cc1] | m-TAZCz |
| 2 | 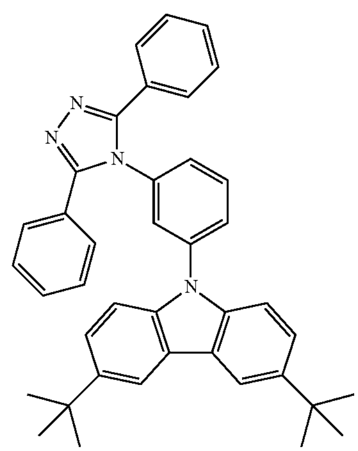 [SMILES: CC(C)(C)c1ccc2c(c1)c1cc(C(C)(C)C)ccc1n2-c1cccc(-n2c(-c3ccccc3)nnc2-c2ccccc2)c1] | m-TAZtCz |
| 3 | 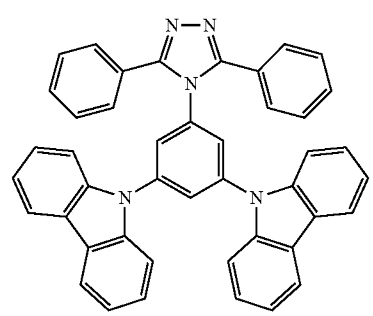 [SMILES: c1ccc(-c2nnc(-c3ccccc3)n2-c2cc(-n3c4ccccc4c4ccccc43)cc(-n3c4ccccc4c4ccccc43)c2)cc1] | m-TAZDCz |

TABLE 1-continued

| Example | Structures | Contraction |
|---|---|---|
| 4 | 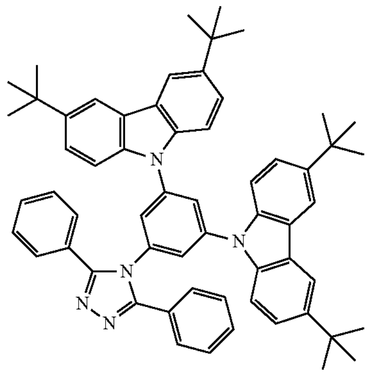 [SMILES: CC(C)(C)c1ccc2c(c1)c1cc(C(C)(C)C)ccc1n2-c1cc(-n2c(-c3ccccc3)nnc2-c2ccccc2)cc(-n2c3ccc(C(C)(C)C)cc3c3cc(C(C)(C)C)ccc32)c1] | m-TAZDtCz |
| 5 | 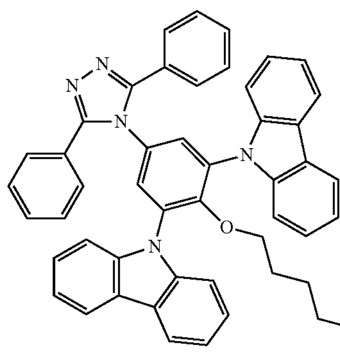 | m-TAZDCz-nH |

In order to clearly illustrate the method for preparing organic compounds of the disclosure, the preparation of compounds disclosed in Examples 1-5 are described in detail as below.

Example 1

Preparation of Compound m-TAZCz

First, compound (1) (benzoyl chloride, 71.42 mmole, 10 g) was added into a 250 ml bottle and dissolved into THF (100 ml). Next, $N_2H_4$ (32.46 mmol, 1.62 g) was injected into the bottle at 0° C. After reacting for 4 hrs, a compound (2) was obtained with a yield of 92%. The synthesis pathway was as follows:

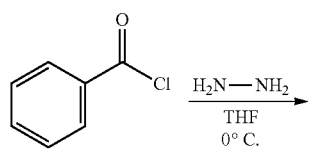

Compound (1)

Compound (2)

Next, compound (2) (41.66 mmol 10 g), and $PCl_5$ (91.51 mmol 18.76 g) were added into a 250 ml bottle and dissolved into toluene (100 mL). Next, after heating to 120° C. for 3 hrs, the result was purified by column chromatography, obtaining compound (3) with a yield of 90%. The synthesis pathway was as follows:

Compound (2)

Compound (3)

Next, compound (3) (18.11 mmol 5 g), 3-bromoaniline (21.73 mmol, 3.69 g), and N,N-dimethyl aniline (25 mL) were added into a 100 ml bottle. Next, after heating to 130° C. for 12 hrs, the result was purified by column chromatography, obtaining compound (4) with a yield of 50%. The synthesis pathway was as follows:

Compound (3)

Compound (4)

Next, compound (4) (8 mmol, 3 g), carbazole (9.6 mmol, 1.61 g) and $K_2CO_3$ (40 mmol, 5.52 g) were added into a 50 ml bottle and dissolved into DMSO (30 ml). The mixture was heated to 180° C. for 36 hrs. After cooling, the result was purified by washing with water, and compound m-TAZCz was obtained. The synthesis pathway was as follows:

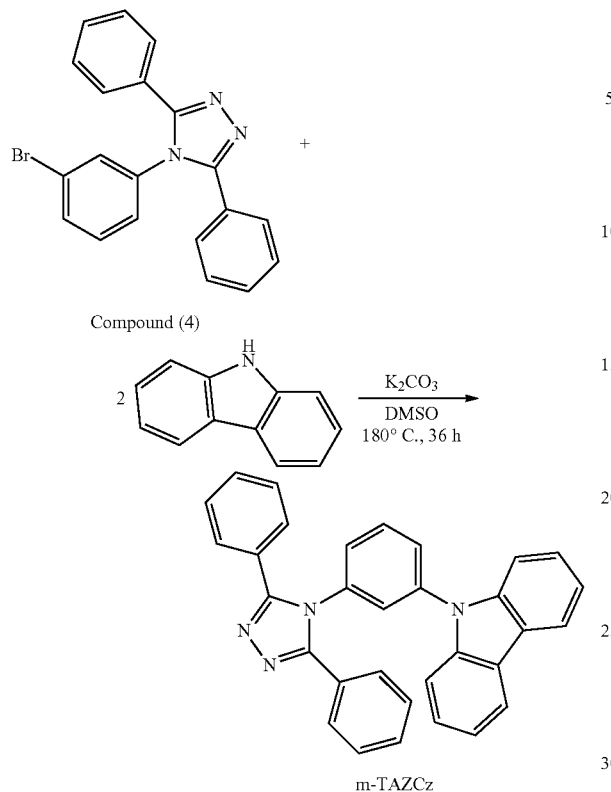

Compound (4)

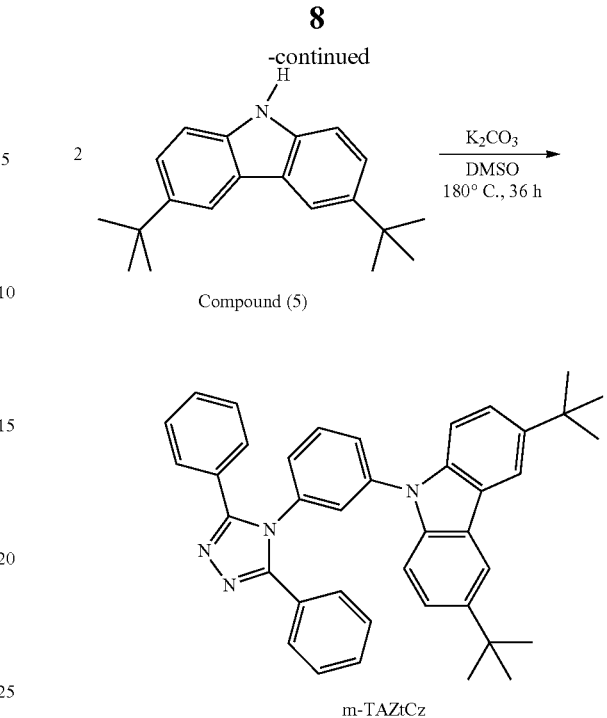

Compound (5)

m-TAZCz m-TAZtCz

The physical measurements of the compound m-TAZCz are listed below:

¹H-NMR (400 MHz, CDCl₃, δ): 8.07 (m, 4H), 7.72-7.21 (m, 20H), 6.85 (m, 4H).
¹³C-NMR (100 MHz, CDCl₃, δ): 154.70, 139.98, 139.38, 136.38, 131.22, 129.92, 129.17, 128.77, 127.42, 126.73, 126.15, 125.93, 123.68, 120.60, 120.44, 109.10.
HRMS (EI) Calcd for $C_{32}H_{22}N_4$ (M⁺): 462.1844. Found: 462.1844.
Elemental analysis: C, 83.09; H, 4.79; N, 12.11. Found: C, 83.33; H, 4.69; N, 12.22.

Example 2

Preparation of Compound m-TAZtCz

Compound (4) (13.33 mmol, 5 g), compound (5) (3,6-di-tert-butyl-9H-carbazole, 16 mmol, 4.46 g) and K₂CO₃ (66.66 mmol, 9.2 g) were added into a 50 ml bottle and dissolved into DMSO (30 ml). The mixture was heated to 180° C. for 36 hrs. After cooling, the result was purified by washing with water, and compound m-TAZtCz was obtained. The synthesis pathway was as follows:

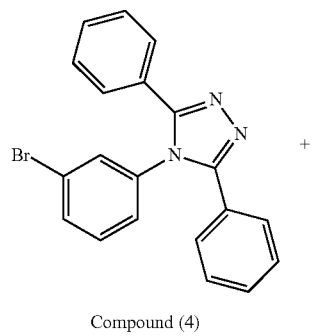

Compound (4)

The physical measurements of the compound m-TAZtCz are listed below:

¹H-NMR (400 MHz, CDCl₃, δ): 8.07 (s, 2H), 7.71-7.16 (m, 16H), 6.84 (d, J=8, 2H), 1.44 (s, 18H).
¹³C-NMR (100 MHz, CDCl₃, δ): 143.69, 138.28, 131.21, 130.06, 129.12, 128.80, 125.38, 123.76, 116.43, 108.58, 34.69, 31.89.
HRMS (EI) Calcd for $C_{40}H_{38}N_4$ (M⁺): 574.3096. Found: 574.3100.
Elemental analysis: C, 83.59; H, 6.66; N, 9.75. Found: C, 83.69; H, 6.74; N, 9.78.

Example 3

Preparation of Compound m-TAZDCz

First, compound (3) (36.22 mmol, 10 g), compound (6) (3,5-difluorobenzenamine, 39.85 mmol, 5.14 g), and N,N-dimethyl aniline (30 mL) were added into a 250 ml bottle. Next, the mixture was heated to 135° C. for 12 hrs. After reaction, a compound (7) was obtained with a yield of 50%. The synthesis pathway was as follows:

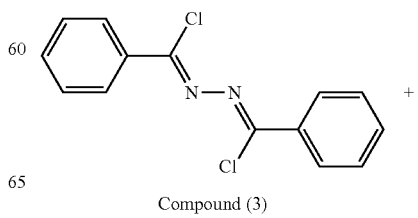

Compound (3)

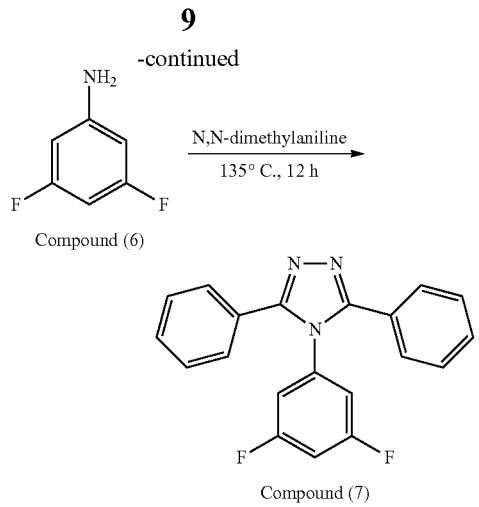

Compound (6)

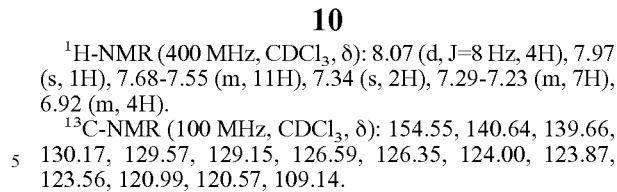

Compound (7)

Next, compound (7) (15.01 mmol, 5 g), carbazole (33.03 mmol, 5.54 g) and K$_2$CO$_3$ (75.05 mmol, 10.35 g) were added into a 50 ml bottle and dissolved into DMSO (30 ml). The mixture was heated to 180° C. for 36 hrs. After cooling, the result was purified by washing with water, and compound m-TAZDCz was obtained with a yield of 82%. The synthesis pathway was as follows:

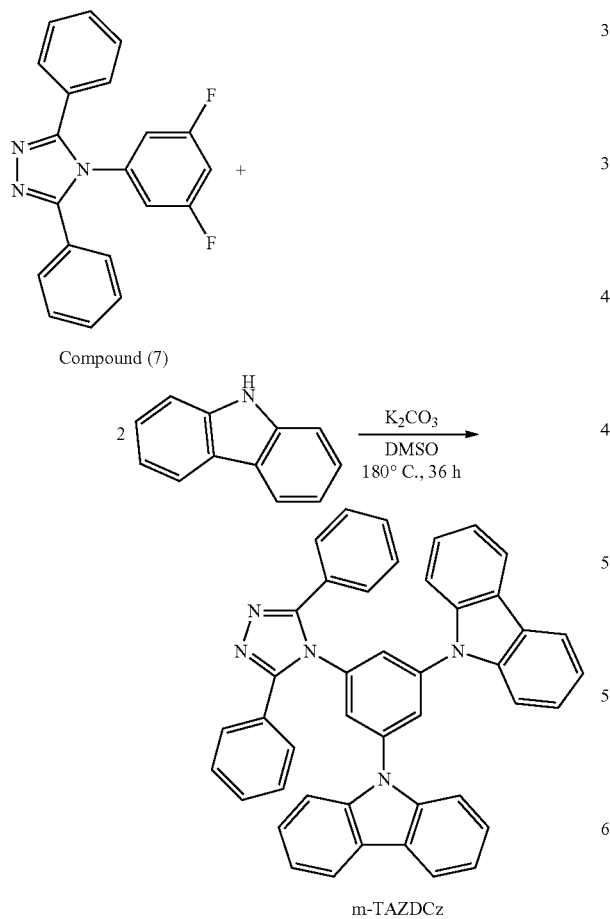

m-TAZDCz

The physical measurements of the compound m-TAZDCz are listed below:

$^1$H-NMR (400 MHz, CDCl$_3$, δ): 8.07 (d, J=8 Hz, 4H), 7.97 (s, 1H), 7.68-7.55 (m, 11H), 7.34 (s, 2H), 7.29-7.23 (m, 7H), 6.92 (m, 4H).

$^{13}$C-NMR (100 MHz, CDCl$_3$, δ): 154.55, 140.64, 139.66, 130.17, 129.57, 129.15, 126.59, 126.35, 124.00, 123.87, 123.56, 120.99, 120.57, 109.14.

HRMS (EI) Calcd for C$_{44}$H$_{29}$N$_5$ (M$^+$): 627.2523. Found: 627.2428. Elemental analysis: C, 84.19; H, 4.66; N, 11.16. Found: C, 84.06; H, 4.69; N, 11.15.

Example 4

Preparation of Compound m-TAZDtCz

Compound (7) (15.01 mmol, 5 g), compound (5) (3,6-di-tert-butyl-9H-carbazole, 33.03 mmol, 9.22 g), and K$_2$CO$_3$ (75.07 mmol, 10.36 g) were added into a 50 ml bottle and dissolved into DMSO (30 ml). The mixture was heated to 180° C. for 36 hrs. After cooling, the result was purified by washing with water, and compound m-TAZDtCz. The synthesis pathway was as follows:

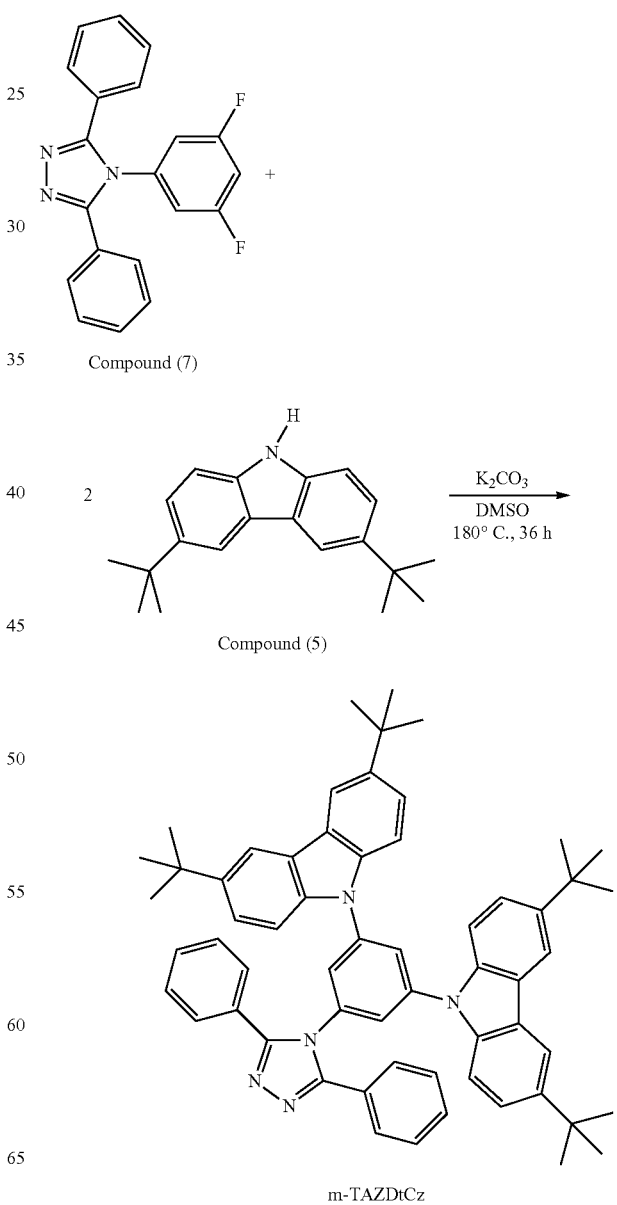

m-TAZDtCz

The physical measurements of the compound m-TAZDtCz are listed below:

$^{1}$H-NMR (400 MHz, CDCl$_{3}$, δ): 8.10 (s, 4H), 8.09 (s, 1H), 7.66-7.28 (m, 16H), 6.89 (m, 4H), 1.47 (s, 36H).

$^{13}$C-NMR (100 MHz, CDCl$_{3}$, δ): 154.71, 144.04, 141.07, 138.02, 137.21, 130.03, 129.49, 129.08, 126.88, 123.97, 123.88, 123.14, 122.58, 116.55, 108.68, 34.71, 31.88.

HRMS (FAB) Calcd for C$_{60}$H$_{61}$N$_{5}$ (M$^{+}$): 851.4927. Found: 851.4928.

Elemental analysis: C, 84.57; H, 7.22; N, 8.22. Found: C, 84.70; H, 7.60; N, 8.29.

Example 5

Preparation of Compound m-TAZDCz-nH

Compound (3) (36.23 mmol, 10 g), compound (8) (4-amino-2,6-difluorophenol, 43.47 mmol, 6.30 g), and N,N-dimethyl aniline were added into a 100 ml reaction bottle. Next, the mixture was heated to 135° C. for 12 hrs. After reaction, a compound (9) was obtained with a yield of 50%. The synthesis pathway was as follows:

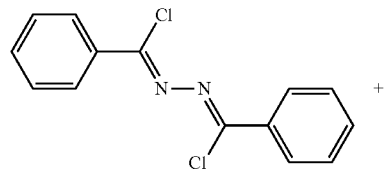

Compound (3)

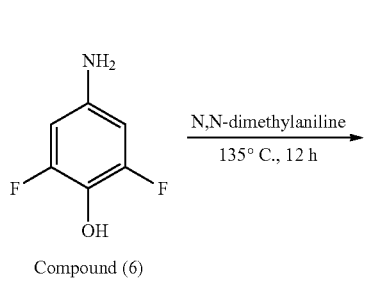

Compound (6)

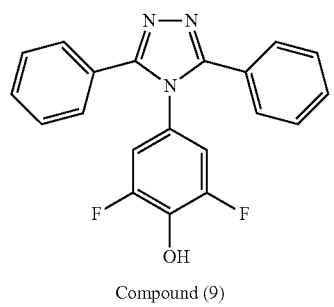

Compound (9)

Compound (9) (14.32 mmol, 5 g), carbazole (31.51 mmol, 5.29 g), and K$_{2}$CO$_{3}$ (71.6 mmol 9.8 g) were added into a 50 ml bottle and dissolved into DMSO (30 ml). The mixture was heated to 180° C. for 36 hrs. After cooling, the result was purified by washing with water, and compound (10) was obtained with a yield of 35%. The synthesis pathway was as follows:

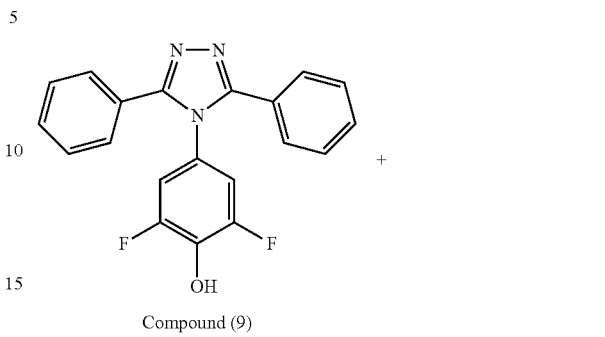

Compound (9)

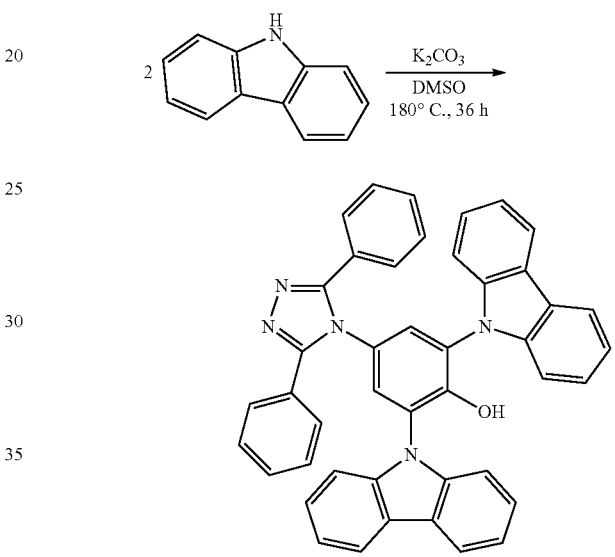

Compound (10)

Next, compound (X) (3.1 mmol, 2 g), 1-Bromohexane (3.73 mmol, 0.61 g), and KOH (4.04 mmol, 0.22 g) were added into a 100 ml bottle and dissolved into ethanol (30 ml). The mixture was heated to reflux for 3 hrs. After purification, compound m-TAZDCz-nH was obtained with a yield of 98%. The synthesis pathway was as follows:

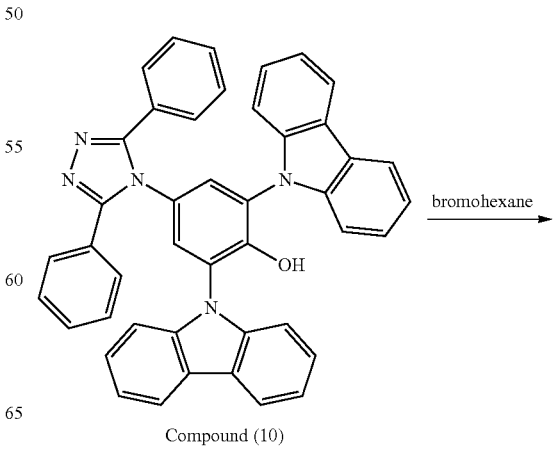

Compound (10)

-continued

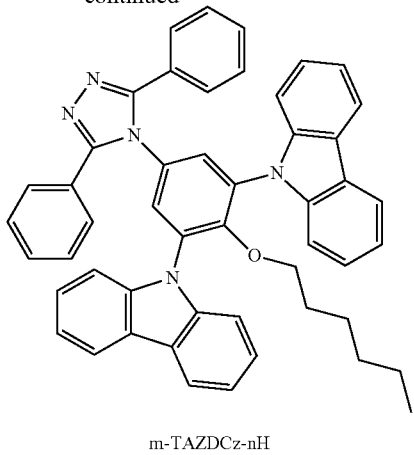

m-TAZDCz-nH

The physical measurements of the compound m-TAZDCz-nH are listed below:

$^1$H-NMR (400 MHz, CDCl$_3$, δ): 8.06 (d, J=8 Hz, 2H), 7.87 (d, 1H), 7.52-7.20 (m, 11H), 6.93 (d, J=8 Hz, 1H), 6.68 (d, J=8 Hz, 2H), 3.93 (t, J$_1$=4 Hz, J$_2$=12 Hz, 2H), 1.42 (m, 2H), 1.03-0.98 (m, 6H), 0.73-0.70 (t, J$_1$=8 Hz, J$_2$=12 Hz).

$^{13}$C-NMR (100 MHz, CDCl$_3$, δ): 155.73, 154.73, 140.55, 129.69, 128.98, 128.58, 128.09, 127.04, 127.06, 126.80, 125.58, 123.29, 120.03, 119.82, 114.11, 109.73, 68.91, 31.06, 28.53, 25.16, 22.20, 13.75.

Properties of Organic Compounds

The glass transition temperature (T$_g$), melting point (T$_m$), decomposition temperature (T$_d$), band gap (E$_S$), triplet energy gap (E$_T$), and HOMO (highest occupied molecular orbital) and LUMO (lowest unoccupied molecular orbital) energy gap of compounds m-TAZCz, m-TAZtCz, m-TAZDCz, and m-TAZDtCz were measured and are shown in Table 2.

TABLE 2

|  | m-TAZCz | m-TAZtCz | m-TAZDCz | m-TAZDtCz |
|---|---|---|---|---|
| T$_g$ | — | 120.6° C. | 159° C. | — |
| T$_m$ | 312.4° C. | 288.7° C. | 301.06° C. | — |
| T$_d$ (5%) | 358° C. | 367° C. | 432° C. | 421° C. |
| LUMO (eV) | 2.31 | 1.92 | 2.03 | 2.13 |
| HOMO (eV) | 5.99 | 5.54 | 5.6 | 5.68 |
| E$_T$ (eV) | 3.0 | 2.99 | 3.01 | 2.97 |
| E$_s$ (eV) | 3.68 | 3.62 | 3.57 | 3.54 |

As shown in Table 2, since the compounds m-TAZCz, m-TAZtCz, and m-TAZDCz have decomposition temperatures (T$_d$) of more than 350° C. (m-TAZDCz has a decomposition temperatures (T$_d$) of more than 430° C. especially), and glass transition temperatures (T$_g$) of more than 120° C., the compounds of the disclosure exhibits excellent thermal stability. The compounds also have suitable LUMO and HOMO energy gaps, thereby substantially matching a normal electron transfer layer.

Organic Electroluminescent Device

FIG. 1 shows an embodiment of an organic electroluminescent device 10. The electroluminescent device 100 includes a substrate 12, a bottom electrode 14, an electroluminescent element 16, and a top electrode 18, as shown in FIG. 1. The organic electroluminescent device can be top-emission, bottom-emission, or dual-emission devices.

The substrate 12 can be a glass plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Further, at least one of the bottom and top electrodes 14 and 18 is transparent.

The electroluminescent element 16 at least includes an emission layer, and can further include a hole injection layer, a hole transport layer, an electron transport layer, and an electron injection layer. In an embodiment of the disclosure, at least one layer of the electroluminescent element 16 includes the aforementioned organic compound.

According to an embodiment of the disclosure, the organic electroluminescent device can be a phosphorescent organic electroluminescent device, and the phosphorescent organic electroluminescent device can include an emission layer including a host material and a phosphorescent dopant, wherein the host material includes the aforementioned organic compounds.

In order to clearly disclose the organic electroluminescent devices of the disclosure, the following examples (using m-TAZCz, m-TAZDCz (prepared from Example 1 and Example 3) as host materials and blue or green phosphorescent dopant) are intended to illustrate the disclosure more fully without limiting their scope, since numerous modifications and variations will be apparent to those skilled in this art.

Example 6

Green Organic Electroluminescent Device

A glass substrate with an indium tin oxide (ITO) film of 100 nm was provided and then washed with a cleaning agent, acetone, and isopropanol with ultrasonic agitation. After drying with nitrogen flow, the ITO film was subjected to a UV/ozone treatment. Next, TAPC (1,1-bis(di-4-tolylaminophenyl)cyclohexane, with a thickness of 40 nm), m-TAZCz doped with Ir(ppy)$_3$ (tris(2-phenylpyridine)iridium) (the ratio between m-TAZCz and Ir(ppy)$_3$ was 100:15, with a thickness of 30 nm), BPhen (4,7-diphenyl-1,10-phenanthroline, with a thickness of 30 nm), LiF (with a thickness of 0.5 nm), and Al (with a thickness of 110 nm) were subsequently formed on the ITO film at 10$^{-6}$ Pa, obtaining the electroluminescent device (1). The materials and layers formed therefrom are described in the following.

ITO (100 nm)/TAPC (40 nm)/15% Ir(ppy)$_3$:m-TAZCz (30 nm)/BPhen (30 nm)/LiF (0.5 nm)/Al (110 nm).

The optical property of the electroluminescent device (1), as described in Example 6, was measured by a PR650 (purchased from Photo Research Inc.) and a Minolta TS110. The results are shown below:

Optimal efficiency: 31.9 cd/A, and 22.7 lm/W;
Emissive efficiency: 31.8 cd/A, and 22.2 lm/W (@1000 cd/m$^2$);
CIE coordinations: (0.30, 0.63).

Example 7

Blue Organic Electroluminescent Device

A glass substrate with an indium tin oxide (ITO) film of 100 nm was provided and then washed with a cleaning agent, acetone, and isopropanol with ultrasonic agitation. After drying with nitrogen flow, the ITO film was subjected to a UV/ozone treatment. Next, NPB (N,N'-di(naphthalene-1-yl)-N,N'-diphenyl-benzidine, with a thickness of 50 nm), TAPC (1,1-bis(di-4-tolylaminophenyl)cyclohexane, with a thickness of 15 nm), m-TAZCz doped with Firpic (Iridium-bis(4,6difluorophenyl-pyridinato-N,C$_2$)-picolinate) (the ratio between m-TAZCz and Ir(ppy)$_3$ was 100:11, with a thickness of 40 nm), m-TPhOXD (Bis(2-tert-butyl-1,3,4-oxadiazole-5-diyl) 3,3'-m-terphenyl, with a thickness of 12.5 nm), BPhen (4,7-diphenyl-1,10-phenanthroline), with a thickness of 12.5 nm), LiF (with a thickness of 1 nm), and Al (with a thickness of 100 nm) were subsequently formed on the ITO film at 10$^{-6}$ Pa, obtaining the electroluminescent device (2). The materials and layers formed therefrom are described in the following.

ITO (100 nm)/NPB (50 nm)/TAPC (15 nm)/m-TAZCz:Firpic 11% (40 nm)/m-TPhOXD (12.5 nm)/BPhen (12.5 nm)/LiF (1 nm)/Al (100 nm)

The optical property of the electroluminescent device (2), as described in Example 7, was measured by a PR650 (purchased from Photo Research Inc.) and a Minolta TS110. The results are shown below:
Optimal efficiency: 21.43 cd/A, 11.99 lm/W;
Emissive efficiency: 20 cd/A, 7.2 lm/W (@1000 cd/m$^2$);
CIE coordinations: (0.16, 0.35).

Example 8

Green Organic Electroluminescent Device

A glass substrate with an indium tin oxide (ITO) film of 100 nm was provided and then washed with a cleaning agent, acetone, and isopropanol with ultrasonic agitation. After drying with nitrogen flow, the ITO film was subjected to a UV/ozone treatment. Next, NPNPB (N,N'-di-phenyl-N,N'-di-[4-(N,N'-diphenyl-amino)phenyl]benzidine, with a thickness of 60 nm), NPB (N,N'-di(naphthalene-1-yl)-N,N'-diphenyl-benzidine, with a thickness of 10 nm), TCTA (4,4',4'-tri (N-carbazolyl)triphenylamine with a thickness of 10 nm), m-TAZDCz doped with Ir(ppy)$_3$ (the ratio between m-TAZCz and Ir(ppy)$_3$ was 100:11, with a thickness of 30 nm), TAZ (3-phenyl-4-(1-naphthyl)-5-phenyl1,2,4-triazole, with a thickness of 10 nm), BAlq (aluminium (III) bis(2-methyl-8-quninolinato)-4-phenylphenolate, with a thickness of 10 nm), LiF (lithium fluoride, with a thickness of 1 nm), and Al (with a thickness of 100 nm) were subsequently formed on the ITO film at 10$^{-6}$ Pa, obtaining the electroluminescent device (3). The materials and layers formed therefrom are described in the following.

ITO (100 nm)/NPNPB (60 nm)/NPB (10 nm)/m-TAZDCz:Ir(ppy)$_3$ (30 nm)/TAZ (10 nm)/BAlq (10 nm)/LiF (1 nm)/Al (100 nm).

NPB (50 nm)/TAPC (15 nm)/m-TAZCz:Firpic 11% (40 nm)/m-TPhOXD (12.5 nm)/BPhen (12.5 nm)/LiF (1 nm)/Al (100 nm)

The optical property of the electroluminescent device (3), as described in Example 8, was measured by a PR650 (purchased from Photo Research Inc.) and a Minolta TS110. The results are shown below:
Optimal efficiency: 93.3 cd/A, 73.3 lm/W;
Emissive efficiency: 88 cd/A, 48 lm/W (@1000 cd/m$^2$);
CIE coordinations: (0.27, 0.65).
Device Lifetime: 1014 hr @ 500 cd/m$^2$ The organic electroluminescent device employing the organic compounds of Formula (I) can have an emissive efficiency of 7 lm/W for emitting blue light (or 48 lm/w for emitting green light) at a brightness of 1000 cd/m$^2$. The green color device lifetime reached to 1014 hours at 500 cd/m$^2$. Accordingly, the organic compounds of Formula (I) of the disclosure have a high triplet energy (tE$_g$) gap and are apt to transmit energy to a guest emitter. The organic compounds of Formula (I) of the disclosure have a triazole moiety bound to the benzene at the meta-position relative to a carbazole moiety resulting in a shorter conjugated system. Therefore, the organic compounds of Formula (I) of the disclosure are suitable as host material of blue or green phosphorescent organic electroluminescent devices, thereby increasing efficiency thereof.

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:
1. An organic compound having a Formula (I), of:

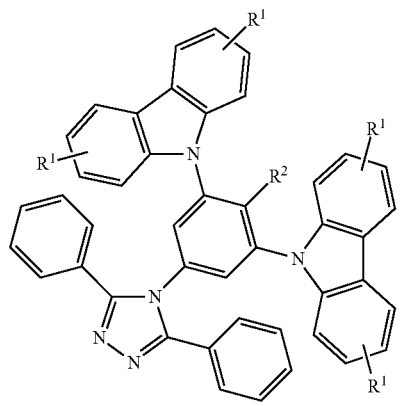

Formula (I)

wherein $R^1$ are independently a hydrogen, or $C_{1-8}$ alkyl; and $R^2$ is a hydrogen, hydroxyl, or $C_{1-8}$ alkoxy.

2. The organic compound as claimed in claim 1, wherein $R^1$ are independently a methyl group, ethyl group, propyl group, isopropyl group, butyl group, tert-butyl group, pentyl group, or hexyl group.

3. The organic compound as claimed in claim 1, wherein $R^2$ is a methoxy group, ethoxy group, propoxy group, isopropoxy group, butoxy group, isobutoxy group, pentyloxy group, or hexyloxy group.

4. The organic compound as claimed in claim 1, wherein the organic compound is

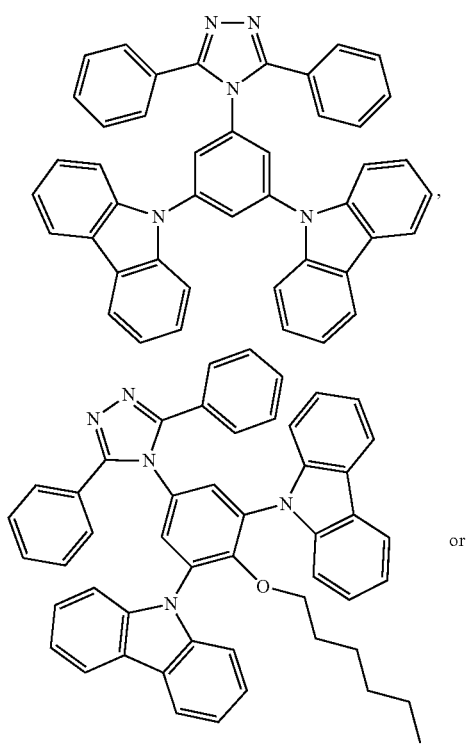

or

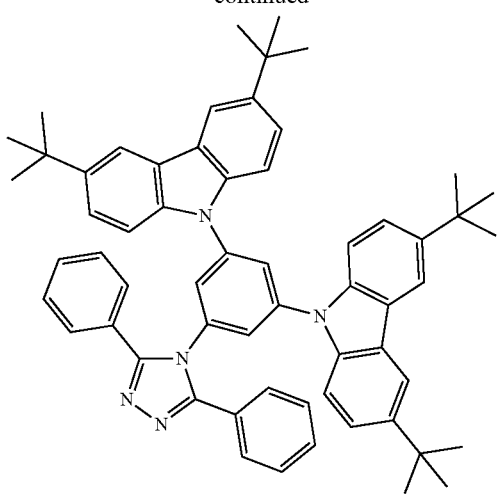

5. An organic electroluminescence device, comprising:

a pair of electrodes; and an electroluminescent element disposed between the pair of electrodes, wherein the electroluminescent element comprises the organic compound as claimed in claim 1.

6. An organic electroluminescence device, comprising:

a pair of electrodes; and an electroluminescent element disposed between the pair of electrodes, wherein the electroluminescent element comprises an emission layer comprising a host material and a phosphorescent dopant, and the host material comprises the organic compound as claimed in claim 1.

7. The organic electroluminescent device as claimed in claim 6, wherein the emission layer emits blue or green light under a bias voltage.

* * * * *